United States Patent
Moon et al.

(10) Patent No.: US 8,444,414 B2
(45) Date of Patent: May 21, 2013

(54) ORTHODONTIC BUCCAL TUBE

(76) Inventors: Seung Soo Moon, Seoul (KR); Sung Hye Moon, Seoul (KR)

( * ) Notice: Subject to any disclaimer, the term of this patent is extended or adjusted under 35 U.S.C. 154(b) by 73 days.

(21) Appl. No.: 13/223,979

(22) Filed: Sep. 1, 2011

(65) Prior Publication Data
US 2012/0129118 A1    May 24, 2012

(30) Foreign Application Priority Data
Nov. 18, 2010   (KR) .................. 10-2010-0115212

(51) Int. Cl.
*A61C 7/16* (2006.01)
(52) U.S. Cl.
USPC .................................. 433/17; 433/9
(58) Field of Classification Search
USPC .............. 433/2, 4, 8, 9, 10, 17, 24, 11
See application file for complete search history.

(56) References Cited

U.S. PATENT DOCUMENTS

| | | | | |
|---|---|---|---|---|
| 4,544,353 A | * | 10/1985 | Maurer et al. | 433/9 |
| 5,522,725 A | * | 6/1996 | Jordan et al. | 433/9 |
| 6,126,441 A | * | 10/2000 | Tenti | 433/17 |
| 6,206,690 B1 | * | 3/2001 | Vargas | 433/9 |
| 2006/0263736 A1 | * | 11/2006 | Moon | 433/9 |

* cited by examiner

*Primary Examiner* — Cris L Rodriguez
*Assistant Examiner* — Justin O'Donnell
(74) *Attorney, Agent, or Firm* — The Webb Law Firm

(57) ABSTRACT

Provided is an orthodontic buccal tube, which is capable of preventing glue from flowing out towards a boundary between a tooth (300) and a base (100), being firmly attached to a face of the tooth (300), and being easily removed from the face of the tooth (300) after being used. The orthodontic buccal tube is attached to the face of the tooth (300) by the glue (400), and includes a base (100) having a bonding face (110) on one side of the buccal tube, a body (200) having a slot (210) into which an archwire is inserted in the middle of the body (200) on a side opposite the base, and a glue anti-outflow step (120) formed along an outer circumference of the bonding face (110) at a predetermined height in a closed loop. The glue anti-outflow step (120) prevents the glue (400) applied to the bonding face (110) from flowing out towards a boundary between the base (100) and the tooth (300).

5 Claims, 2 Drawing Sheets

ORTHODONTIC BUCCAL TUBE

BACKGROUND OF THE INVENTION

1. Field of the Invention

The present invention relates, in general, to an orthodontic buccal tube, and, more particularly, to an orthodontic buccal tube capable of preventing glue from flowing out towards a boundary between a tooth and a base, being firmly attached to a face of the tooth, and being easily removed from the face of the tooth after being used.

2. Description of the Related Art

Generally, methods of correcting irregularities in the teeth using orthodontic brackets and buccal tubes are widely known. In these methods, the orthodontic brackets or buccal tubes are anchored to the faces of the teeth, and then the orthodontic brackets and buccal tubes are interconnected by an archwire, so that irregularities in the teeth are corrected by the force generated by the archwire.

The orthodontic brackets are bonded to the incisors. The orthodontic bracket is typically made up of a base having a bonding face that is attached to the face of the tooth using glue, and a body having a slot that is formed on a side opposite the bonding face of the base and holds an archwire.

The orthodontic buccal tubes are bonded to the molars (e.g., first or second molars). An example of a conventional orthodontic buccal tube is shown in FIG. 1. The orthodontic buccal tube is made up of a base 10 and a body 20, the same as is the orthodontic bracket. The base 10 includes a protrusion 30 on one side thereof so as to correspond to a curved shape of the molar, and the body 20 includes a ball hook 40 used along with an elastic part or other characteristic part of an orthodontic brace.

The orthodontic buccal tube is attached to the tooth by applying glue to the bonding face 11 of the base 10 thereof. In this case, when the glue flows out and hardens at a boundary between the base 10 and the tooth, the boundary between the base and the tooth is discolored by the time orthodontic treatment is completed.

Further, like the orthodontic bracket, the orthodontic buccal tube should be firmly attached to the face of the tooth for an orthodontic treatment period, and be able to be easily separated from the face of the tooth after being used. As such, in the case of the conventional orthodontic buccal tube, the bonding face of the base is formed so as to be uneven, and a mesh is fused to the uneven face so as to enhance the bonding strength. However, when only the bonding strength of the bonding face is emphasized in this way, the orthodontic buccal tube is not easily separated from the face of the tooth after the orthodontic treatment is completed. Even if so, many residuals are left on the face of the tooth. In other words, the orthodontic buccal tube is not separated clearly.

Further, the conventional orthodontic buccal tube is picked up with a tool such as a pincette or tweezers to be attached. Since no structure is provided to catch the conventional orthodontic buccal tube, the conventional orthodontic buccal tube slips off the tool.

SUMMARY OF THE INVENTION

Accordingly, the present invention has been made keeping in mind the above problems occurring in the related art, and an objective of the present invention is to provide an orthodontic buccal tube that prevents glue from flowing out towards a boundary between a tooth and a base, that is firmly attached to a face of the tooth, that is easily removed from the face of the tooth after being used, and that is reliably picked up without slipping using a tool such as a pincette or tweezers.

In order to achieve the above objective, according to one aspect of the present invention, there is provided an orthodontic buccal tube attached to the face of a tooth by glue. The orthodontic buccal tube includes: a base having a bonding face on one side of the buccal tube; a body having a slot into which an archwire is inserted in the middle of the body on a side opposite the base; and a glue anti-outflow step formed along an outer circumference of the bonding face in a closed loop having a predetermined height. The glue anti-outflow step prevents the glue applied to the bonding face from flowing out towards the boundary between the base and the tooth.

Here, the bonding face may include a plurality of pimples arranged within an area surrounded by the glue anti-outflow step at regular intervals and at a predetermined height.

Further, the glue anti-outflow step may have a shape including a shape of the peripheral pimple at a region where a position of each of the peripheral pimples arranged at regular intervals is superimposed on that of the glue anti-outflow step.

The plurality of pimples may be divided into a central pimple that is located at the center of the bonding face and peripheral pimples that are located around the central pimple, and the contact area of the central pimple may be formed to be larger than that of each peripheral pimple without overlapping with the arrangement of the peripheral pimples.

Here, the central pimple may be greater in height than the glue anti-outflow step and each peripheral pimple.

Further, the height of the central pimple may be higher than that of the glue anti-outflow step and that of each peripheral pimple by about 0.1 mm.

Meanwhile, the body may include a pair of recesses formed on left and right sides of the slot thereof, and each recess may be configured so that left and right sides thereof are inclined at a predetermined angle so as to have a trapezoidal cross section when viewed from the top.

Further, the inclined angle of each of the left and right sides of the recess may be 20 degrees.

According to the orthodontic buccal tube described above, the following effects can be obtained.

The glue anti-outflow step is formed along an outer circumference of the bonding face of the base, so that the glue can be prevented from flowing out towards the boundary between the base and the tooth. Thus, the boundary between the base and the tooth can be prevented from being discolored.

A plurality of pimples are formed on the bonding face of the base. Thus, when the orthodontic buccal tube is attached to the face of the tooth using glue, an area over which the glue is applied to the base is increased, so that the orthodontic buccal tube can be firmly attached to the face of the tooth.

Among the plurality of pimples formed on the bonding face of the base, a central pimple located at the center of the base is formed to have a larger contact area than the other pimples. Thus, when the orthodontic buccal tube is removed from the face of the tooth, the central pimple is separated first, so that the orthodontic buccal tube can be easily removed from the face of the tooth.

The body has a pair of recesses formed on both sides thereof. Each recess is configured so that left and right sides thereof are inclined at a predetermined angle so that each recess has a trapezoidal cross section when viewed from the top. Thus, the body of the orthodontic buccal tube can be reliably picked up without slipping when using a tool such as a pincette or tweezers.

BRIEF DESCRIPTION OF THE DRAWINGS

The above and other objectives, features and advantages of the present invention will be more clearly understood from the following detailed description when taken in conjunction with the accompanying drawings, in which.

DETAILED DESCRIPTION OF THE INVENTION

Reference will now be made in greater detail to an exemplary embodiment of the invention with reference to the accompanying drawings.

Figure 1:
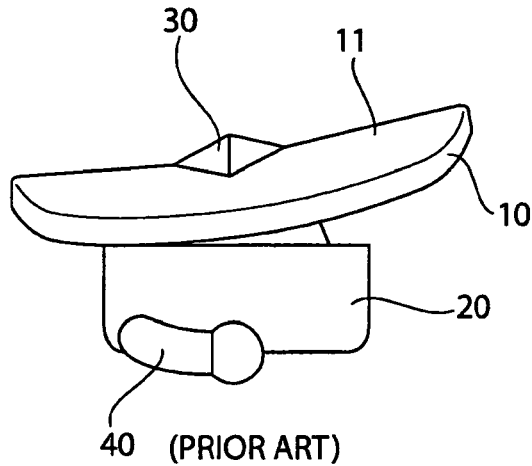
FIG. 1 shows an example of a conventional orthodontic buccal tube.
Figure 2:
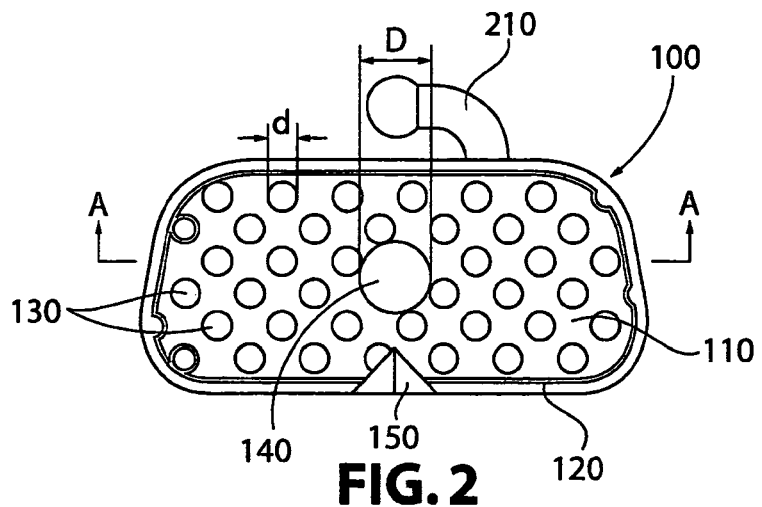
FIG. 2 shows a base of an orthodontic buccal tube according to an exemplary embodiment of the invention.
Figure 3:
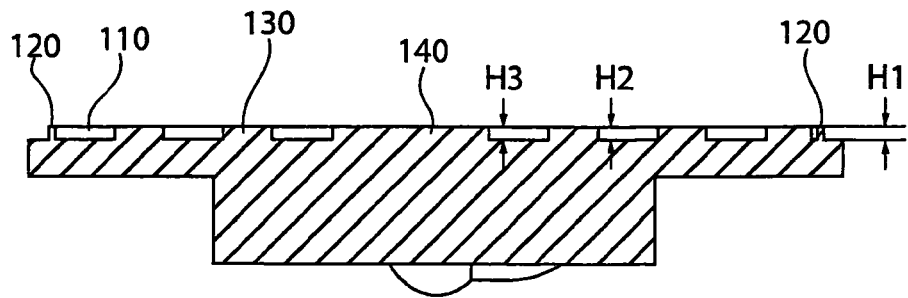
FIG. 3 is a cross-sectional view taken along line A-A of FIG. 2.
Figure 4:
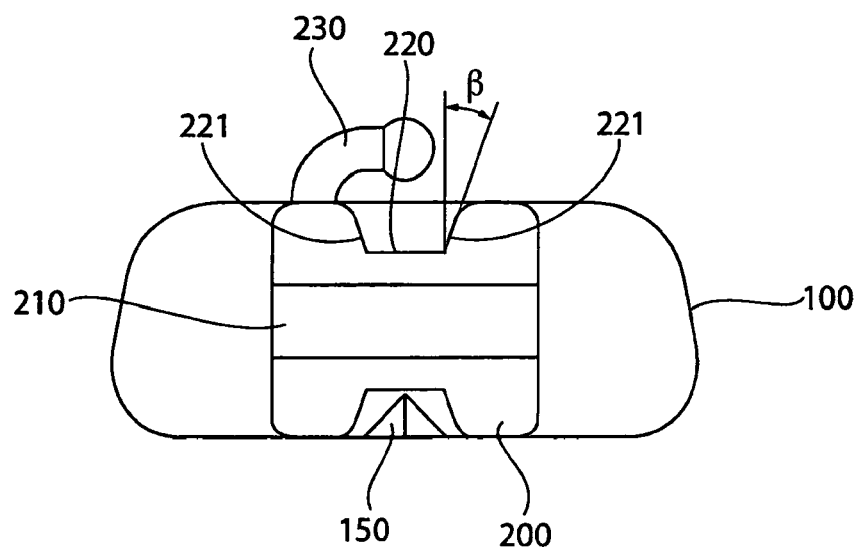
FIG. 4 shows a body of the orthodontic buccal tube according to the exemplary embodiment of the invention.
Figure 5:
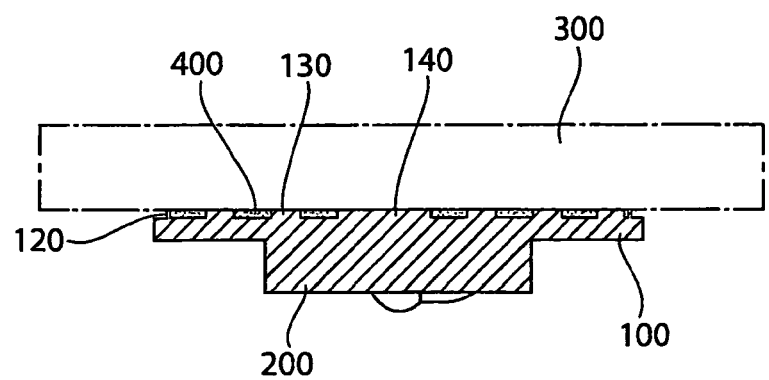
FIG. 5 shows how the orthodontic buccal tube according to the exemplary embodiment of the invention is attached to the face of a tooth.

FIG. 2 shows an orthodontic buccal tube according to an exemplary embodiment of the invention, and FIG. 3 is a cross-sectional view taken along line A-A of FIG. 2. FIG. 4 shows a body of the orthodontic buccal tube according to the exemplary embodiment of the invention, and FIG. 5 shows how the orthodontic buccal tube according to the exemplary embodiment of the invention is attached to the face of a tooth.

Referring to FIGS. 2 to 5, the orthodontic buccal tube according to the exemplary embodiment of the invention includes a base 100 and a body 200.

The base 100 has a rectangular shape, and preferably a trapezoidal shape. The base 100 may be formed in a variety of sizes and shapes depending on the size and shape of a tooth to which it is to be bonded.

The base 100 is provided with a bonding face 110 bonded to the face of the tooth by glue 400. The bonding face 110 of the base 100 is curved similarly to the face of the tooth. The bonding face 110 of the base 100 may have another curved face depending on the tooth to be bonded. The bonding face 110 of the base 100 is provided with a protrusion 150 on one side thereof that corresponds to the curved shape of a molar.

Meanwhile, the bonding face 110 of the base 100 is provided with a glue anti-outflow step 120 that prevents the glue 400 applied to the bonding face 110 from flowing out toward a boundary between the base 100 and the tooth. The glue anti-outflow step 120 is formed along an outer circumference of the base 100 in a closed loop having a predetermined height. Thus, the glue 400 applied to the bonding face 110 of the base 100 does not flow out toward the boundary between the base 100 and the tooth when the orthodontic buccal tube is bonded to the tooth.

Further, a plurality of pimples is formed within an area surrounded by the glue anti-outflow step 120 of the bonding face 110 of the base 100 at regular intervals and at a predetermined height. The plurality of pimples are divided into a central pimple 140 located at the center of the bonding face 110, and a plurality of peripheral pimples 130 located around the central pimple. The contact area of the central pimple 140 is formed so as to be larger than that of the peripheral pimples 130 without overlapping with the arrangement of the peripheral pimples 130.

In detail, when the central pimple 140 and each peripheral pimple 130 are formed so as to have a circular cross section as shown in FIG. 2, the central pimple 140 is preferably configured so that its diameter D is larger than that d of each peripheral pimple 130 and is increased to a large enough size to be put in contact with the peripheral pimples 130 located around the central pimple.

The reason the plurality of pimples are formed on the bonding face 110 of the base 100 is to increase an area over which the glue 400 is applied to the base 100 to secure firm bonding between the buccal tube and the tooth.

Further, the reason the diameter D of the central pimple 140 is increased in order to make a contact area of the central pimple 140 larger than that of each peripheral pimple 130 is to make the amount of the glue 400 applied to the central pimple 140 smaller than that applied to each peripheral pimple 130 and to leave a space between the peripheral pimples 130, thereby ensuring that the central pimple 140 separates first when the buccal tube is removed from the face of the tooth. In this way, when the central pimple 140 is the first to separate, the separation is propagated to the peripheral pimples 130 adjacent to the central pimple 140, so that the buccal tube can be easily removed from the face of the tooth.

Meanwhile, a height H1 of the glue anti-outflow step 120, a height H2 of the peripheral pimple 130, and a height H3 of the central pimple 140 are equal to one another. However, the height H3 of the central pimple 140 is preferably greater than the height H1 of the glue anti-outflow step 120 and the height H2 of the peripheral pimple 130 by about 0.1 mm so that the separation easily starts from the central pimple 140 when the buccal tube is removed from the face of the tooth. In this manner, when the height H3 of the central pimple 140 is higher than the height H1 of the glue anti-outflow step 120 and the height H2 of the peripheral pimple 130, the amount of glue 400 applied to the central pimple 140 is further reduced, so that the separation occurs in an easier manner. However, when a difference between the height of the central pimple 140 and the height of the glue anti-outflow step 120 or the peripheral pimple 130 is more than 0.1 mm, the bonding strength is remarkably reduced at the central pimple 140. Accordingly, the difference in height preferably does not exceed 0.1 mm.

Further, at a region where a position of each of the peripheral pimples 130 arranged at regular intervals is superimposed on that of the glue anti-outflow step 120, the glue anti-outflow step 120 preferably has a shape including a shape of the peripheral pimple. This is to solve the problem of, if no peripheral pimple 130 is provided within regions where the positions of the peripheral pimples 130 are superimposed on the position of the glue anti-outflow step 120, the bonding strength being less strong at a region where no peripheral pimple 130 is provided. This is furthermore to prevent the separation from the central pimple 140 from discontinuously propagating to the peripheral pimples 130 when the buccal tube is removed from the face of the tooth.

Now, referring to FIG. 4, the body 200 is continuously formed on a side opposite the bonding face 110 of the base 100. The body 200 is provided with a slot 210 in the middle thereof into which an archwire (not shown) is inserted. The slot 210 is formed so as to have enough width and depth for archwire to fit therein. The body 200 is provided with a ball hook 230 on one side thereof which is used along with an elastic part or other characteristic parts of an orthodontic brace.

Further, the body 200 has a pair of recesses 220 formed on left and right sides thereof centering the slot 210. Each recess 220 is configured so that one side thereof is open to one side of the body 200, and so that left and right sides 221 thereof are inclined at a predetermined angle β so as to have a trapezoidal cross section when viewed from the top. Here, the inclined C angle β of the left and right sides 221 is preferably 20 degrees. When the inclined angle β is 10 degrees, the body 200 still slips when it is picked up with a tool such as a pincette or tweezers. When the inclined angle β is 30 degrees, the tool interferes with the ball hook 230.

Hereinafter, the operation of the orthodontic buccal tube, having the aforementioned configuration, according to the exemplary embodiment of the invention will be described in detail.

Referring to FIG. 5 along with FIGS. 2 to 4 described above, the orthodontic buccal tube is anchored to the face of a tooth 300 via glue 400 selected by an orthodontist or its manufacturer.

When the glue 400 is applied to a central portion of the base 100, the glue 400 is filled inside the glue anti-outflow step 120 formed on the bonding face 110 of the base 100, and covers the bonding face 110 and proceeds up a predetermined height. Here, the glue 400 covering between the central pimple 140 and the peripheral pimples 130 on the bonding face 110 has the same depth as the glue 400 covering the top of the central pimple 140 and the peripheral pimples 130. After the glue 400 has been applied to the base 100 in this way, the orthodontic buccal tube is picked up with a tool such as a pincette or tweezers. In this case, the orthodontic buccal tube can be reliably picked up without slipping due to a pair of recesses 220 formed in the body 200. When the orthodontic buccal tube is pressurized in order to attach it to the tooth 300, the glue 400 applied to the base 100 spreads toward an edge of the bonding face 110. In this case, the glue 400 is prevented from flowing out toward a boundary between the base 100 and the tooth 300 due to the glue anti-outflow step 120 formed on the bonding face 110.

In this manner, after the orthodontic buccal tube has been anchored to the face of the tooth 300, orthodontic treatment is performed using typical methods.

When the orthodontic buccal tube is anchored to the face of the tooth 300 in this way, the glue 400 covering the area between the central pimple 140 and the peripheral pimples 130 on the bonding face 110 is integrated with the glue 400 covering the top of the central pimple 140 and the peripheral pimples 130, and then is bonded to and cured on the face of the tooth 300.

In this case, an area where the glue 400 is applied to the bonding face 110 of the base 100 is considerably increased compared to the case where the central pimple 140 and the peripheral pimples 130 are not formed on the bonding face 110, so that the orthodontic buccal tube can be firmly bonded to the face of the tooth 300.

Meanwhile, after several months or years have elapsed and orthodontic treatment has finished, the orthodontic buccal tube is removed from the face of the tooth. Even before the orthodontic treatment has completed, the orthodontic buccal tube may be removed from the face of the tooth as needed. In either case, when an external force is applied to the orthodontic buccal tube using a removal tool (not shown), the central pimple 140 where an amount of the applied glue 400 is small is the first to separate. As separation first occurs from the central pimple 140, the separation propagates to the peripheral pimples 130 adjacent to the central pimple 140, so that the buccal tube can be easily removed from the face of the tooth 300.

Although an exemplary embodiment of the invention has been described for illustrative purposes, those skilled in the art will appreciate that various modifications, additions and substitutions are possible, without departing from the scope and spirit of the invention as disclosed in the accompanying claims.

What is claimed is:

1. An orthodontic buccal tube attached to a face of a tooth by glue, comprising:
a base having a bonding face on one side of the buccal tube;
a body having a slot into which an archwire is inserted in a middle of the body on a side opposite the base; and
a glue anti-outflow step formed along an outer circumference of the bonding face at a predetermined height in a closed loop, the glue anti-outflow step preventing the glue applied to the bonding face from flowing out towards a boundary between the base and the tooth,
wherein the bonding face includes a plurality of pimples arranged within an area surrounded by the glue anti-outflow step at regular intervals and at a predetermined height,
wherein the plurality of pimples are divided into a central pimple that is located at a center of the bonding face and peripheral pimples that are located around the central pimple, and the central pimple is formed so as to have a larger contact area than each peripheral pimple without overlapping with an arrangement of the peripheral pimples, and
wherein the central pimple has a height greater than the glue anti-outflow step and each peripheral pimple so that the separation starts from the central pimple when the buccal tube is removed from the face of the tooth;
wherein the height of the pimples and the glue anti-outflow step is measured vertically from the bonding face.

2. The orthodontic buccal tube according to claim 1, wherein the glue anti-outflow step has a shape including a shape of the peripheral pimple at a region where a position of each of the peripheral pimples arranged at regular intervals is superimposed on that of the glue anti-outflow step.

3. The orthodontic buccal tube according claim 1, wherein the height of the central pimple is greater than that of the glue anti-outflow step and that of each peripheral pimple by 0.1 mm.

4. The orthodontic buccal tube according to claim 1, wherein the body includes a pair of recesses formed on left and right sides of the slot thereof, and each recess having an adjacent left and right side, each side inclined with respect to the recess at a predetermined angle so as to have a trapazoidal cross section when viewed from the top.

5. The orthodontic buccal tube according to claim 4, wherein the predetermined angle of each of the left and right sides of the recess is 20 degrees.

* * * * *

UNITED STATES PATENT AND TRADEMARK OFFICE
CERTIFICATE OF CORRECTION

PATENT NO. : 8,444,414 B2
APPLICATION NO. : 13/223979
DATED : May 21, 2013
INVENTOR(S) : Seung Soo Moon et al.

It is certified that error appears in the above-identified patent and that said Letters Patent is hereby corrected as shown below:

In the Claims

Column 6, Line 45, Claim 3, delete "according" and insert -- according to --

Column 6, Line 53, Claim 4, delete "trapazoidal" and insert -- trapezoidal --

Signed and Sealed this
Twenty-seventh Day of August, 2013

Teresa Stanek Rea
*Acting Director of the United States Patent and Trademark Office*